United States Patent [19]

Gilbard et al.

[11] Patent Number: 4,753,945
[45] Date of Patent: Jun. 28, 1988

[54] STIMULATION OF TEAR SECRETION WITH PHOSPHODIESTERASE INHIBITORS

[75] Inventors: Jeffrey P. Gilbard, Boston; Darlene A. Dartt, Newton, both of Mass.

[73] Assignee: Eye Research Institute of Retina Foundation, Boston, Mass.

[21] Appl. No.: 830,997

[22] Filed: Feb. 19, 1986

[51] Int. Cl.$^4$ .............................................. A61K 31/52
[52] U.S. Cl. ..................................... 514/263; 514/912; 424/450
[58] Field of Search ................................ 514/263, 912

[56] References Cited

U.S. PATENT DOCUMENTS

| | | | |
|---|---|---|---|
| 4,208,406 | 6/1980 | Lapinet et al. | 424/180 |
| 4,478,822 | 10/1984 | Haslam et al. | 514/263 |
| 4,544,556 | 10/1985 | Fedi et al. | 514/263 |
| 4,559,343 | 12/1985 | Han et al. | 514/914 |
| 4,717,713 | 1/1988 | Zatz et al. | 514/263 |

FOREIGN PATENT DOCUMENTS

| | | | |
|---|---|---|---|
| 185331 | 6/1986 | European Pat. Off. | 514/263 |
| 897492 | 2/1984 | Fed. Rep. of Germany | 514/263 |
| 2358155 | 2/1978 | France | |
| 932847 | 7/1963 | United Kingdom | 514/263 |
| 1561037 | 2/1980 | United Kingdom | |
| 2078518 | 1/1982 | United Kingdom | 514/263 |
| 2164556 | 3/1986 | United Kingdom | 514/263 |

OTHER PUBLICATIONS

Chem. Abst. 98:173178V (1983)-Aleksecv et al.
Chem. Abst. 103:154063e (1985)-Green et al.
"Cyclic Nucleotide-Dependant Enzyme Secretion in the Rat Lacrimal Gland" Dartt, et al., J. Physiol. (1984), 352, pp. 375-384.
"Effects of Xanthine Derivatives on Lipolysis and on Adenosine 3'-5' Monophosphate Activity" Beavo, et al., Molecular Pharm., vol. 6, No. 6, pp. 597-603, Nov. 1970.
"Alph-Adrenergic Pathway for Stimulation of Lacrimal Gland Protein Secretion" Cornea Conference, 11/1 & 11/2/85, Dartt et al.
"Vasoactive Intestinal Polypeptide Stimulation of Protein Secretion from Rat Gland Acini" Am. J. Physiol. 247:G502-G509, (1984), Dartt et al.
"Receptor for Secretagogues on Pancreatic Acinar Cells" J. of Physiol. 238:G63-G66 (1980), Gardner and Jensen.
"Adrenocorticotropic Hormone and Alpha-Melanocyte-Stimulating Hormone Induce Secretion and Protein Phosphorylation in the Rat Lacrimal Gland by Activation of a cAMP-Dependent Pathway", Eur. J. Biochem., 126:623-629, (1982), Jahn et al.
"Ultrastructural Localization of VIP-like Immunoreactivity in Large Dense-Core Vesicles of Cholinergic-Type Nerve Terminals in Cat Exocrine Glands" Neuroscience 6:847-862, (1981), Johansson and Lundberg.
"Vasoactive Intestinal Peptide Stimulates Outward Current in Single Lacrimal Acini Cells from Rat" Supplement to Investigative Ophthalmology & Visual Science, 27(3) Mar. 1986, Lechleiter et al.
"Effect of Different Secretagogues on Lacrimal Protein Pattern", (International Tear Film Symposiu, 1984, Lubbock, Tex.) Stolze and Somer.
"Influence of Secretagogues on Volume and Protein Pattern in Rabbit Lacrimal Fluid" Current Eye Re- (List continued on next page.)

Primary Examiner—Douglas W. Robinson
Attorney, Agent, or Firm—Lahive & Cockfield

[57] ABSTRACT

A method and preparation for the stimulation of tear secretion. The method involves topically applying a phosphodiesterase inhibitor and/or cyclic nucleotide analogue to the ocular surface. Inhibition of phosphodiesterase and cyclic nucleotide analogues increase cyclic nucleotide levels in lacrimal gland tissue, thereby stimulting tear secretion. The preparation contains a phosphodiesterase inhibitor or a cyclic nucleotide analogue and a vehicle for the phosphodiesterase inhibitor or cyclic nucleotide analogue, and may contain an ophthalmic preservative.

6 Claims, 3 Drawing Sheets

OTHER PUBLICATIONS search, vol. 4 No. 4, pp. 489–492 (1985), Stolze and Sommer.

"Stimulation of Retinol Secretion in Lacrimal Gland Fluid by Acetylcholine and Vasoactive Intestinal Peptide (VIP)" (Cornea Conference, 11/1 & 11/2/85) Ubels et al.

"Correlation of Secretion of Retinol and Protein by the Lacrimal Gland" Supplement to Investigative Ophthalmology & Visual Science 27(3), Mar. 1986, Ubels et al.

"Vasoactive Intestinal Peptide Nerves in Ocular Structures of the Cat" Invest. Ophthlamol. Vis. Sci. 19:878–885 (1980), Uddmen et al.

"A New Generation of Phosphodiesterases Inhibitors: Multiple Molecular Forms of Phosphodiesterases and the Potential for Drug Selectivity" Journal of Medicinal Chemistry, vol. 28, No. 5, May 1985, Weishaar et al.

Dartt et al., Lacrimal Gland Electrolyte and Water Secretion in the Rabbit: Localization and Role of $(Na^+ + K^+)$ activated ATPase, J. Physiol. (1981), 321:559–569.

Dartt, Cellular Control of Protein Electrolyte, and Water Secretion by the Lacrimal Gland, In *The Preoccular Tear Film in Health, Disease and Contact Lens Wear*, (F. J. Holly, ed.), Dry Eye Institute, Inc., Lubbock, Tex. (1986), pp. 358–370.

Friedman et al., B-Adrenergic Receptor Stimulated Peroxide Secretion from Rat Lacrimal Gland, Biochim. Biophys. Acta, (1981), 675:40–45.

Gilbard and Dartt, Changes in Rabbit Lacrimal Gland Fluid Osmolarity with Flow Rate, Invest. Ophthalmoh. Vis. Sci. (1981), 23:804–806.

Mauduit et al., Protein Secretion Induced by Isoproterenol or Pentoxifylline in Lacrimal Gland: $Ca^{2+}$ effects, Am. J. Physiol. (1984), 246:C37–C44.

Stolze and Sommer, Effect of different scretagogues in rabbit lacrimal gland protein secretion, in *The Preoccular Tear Film in Health, Disease and Contact Lens Wear*, (F. J. Holly, ed.), Dry Eye Institute, Inc., Lubbock, Tex. (1986), pp. 409–416.

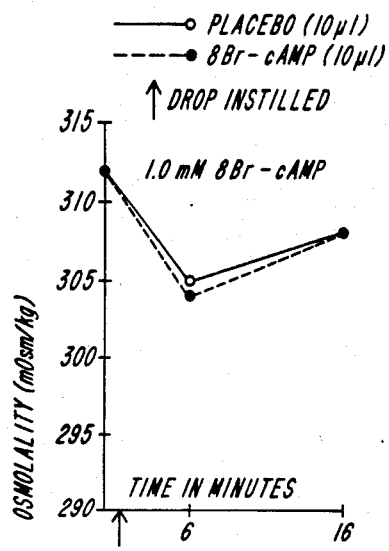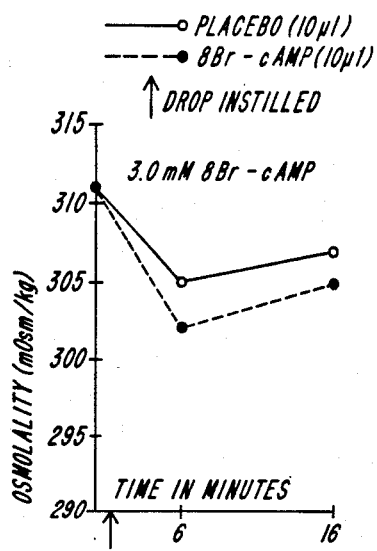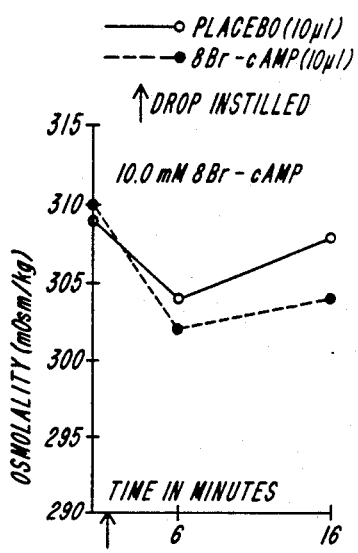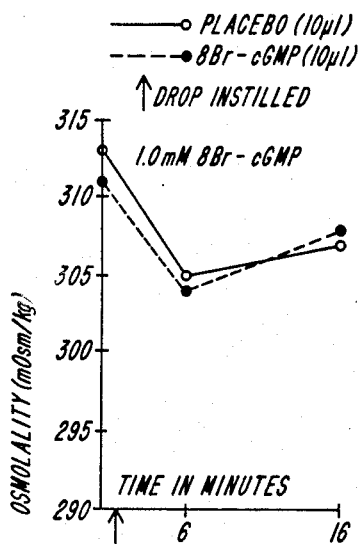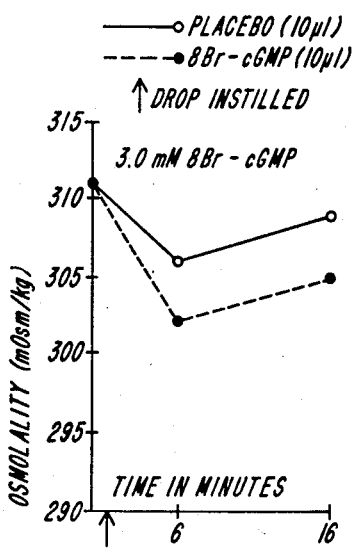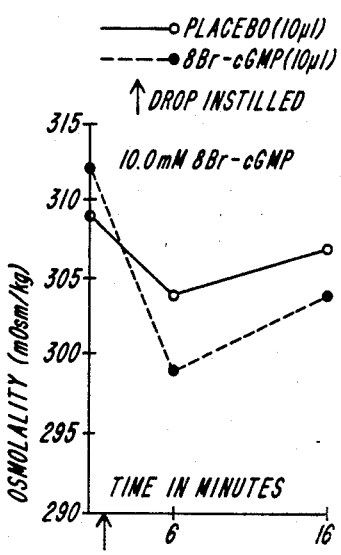

STIMULATION OF TEAR SECRETION WITH PHOSPHODIESTERASE INHIBITORS

BACKGROUND OF THE INVENTION

This invention was made with Government support under EYO3373 awarded by the National Eye Institute and the Federal Government has limited rights therein.

This invention relates to a method and preparation for stimulating tear secretion. More particularly, it relates to the stimulation of tear secretion with topically applied agents including certain phosphodiesterase inhibitors and certain cyclic nucleotide analogues that increase intracellular cyclic nucleotide levels in lacrimal gland tissue.

There are a number of situations where it is desirable to increase the amount and/or to modify the nature of tear fluid produced by the eye. Illustrative instances include the treatment of a spectrum of dry eye disorders including, but not limited to, keratoconjunctivitis sicca, age-related dry eye, Stevens-Johnson syndrome, ocular cicatricial pemphigoid, blepharitis, neurotrophic ocular surface disease and corneal exposure. In addition, patients who wear contact lenses may have sub-optimal rates of tear production for optimal contact lens wear. Increased tear production is likely to increase eye comfort and contact lens comfort, and improve contact lens wear. These patients will therefore benefit from agents that increase tear production.

The lacrimal gland is an exocrine gland which secretes protein and, by different mechanisms, water and electrolytes. To stimulate secretion, agonists are employed which increase intracellular free calcium concentration, and/or the concentration of adenosine 3', 5'-cyclic monophosphate (cyclic AMP or cAMP). However, proteins are secreted by exocytosis, whereas electrolytes and water are secreted as the permeability of cell membranes is selectively increased to sodium, potassium and chloride. A given agonist could stimulate water and electrolyte secretion, but not protein secretion, and visa versa.

The cyclic nucleotides, cyclic AMP, and guanosine 3', 5'-cyclic monophosphate (cyclic GMP or cGMP) are known to regulate a variety of metabolic processes. Cyclic AMP has been suggested to function as a second messenger for exocytosis in the lacrimal gland. Phosphodiesterases are enzymes responsible for the destruction of cyclic AMP by catalyzing the hydrolytic reaction of cyclic AMP and water to produce adenosine 5'-monophosphate and for the destruction of cyclic GMP by catalyzing the hydrolytic reaction of cyclic GMP and water to produce guanosine 5'-monophosphate.

Various molecular forms of phosphodiesterase are distributed in tissues and cells. Agents that inhibit phosphodiestereases may produce tissue selective responses (Weishaur, R. E. et al J. of Med. Chem. 28; 537–545, 1985).

It is known that the phosphodiesterase inhibitors theophylline, 3-isobutyl-1-methylxanthine (IBMX), and pentoxfylline increase cyclic AMP levels in lacrimal gland cells and stimulate protein secretion from lacrimal gland tissue pieces or cells in vitro (Friedman Z. Y. et al, Biochemica et Biophysica Acta 675: 40–45, 1981: Jahn R. et al, Eur. J. Biochem 126: 623–629, 1982; Mauduit P. et al, Am J. Physiol J. 246; C37–C44, 1984; Dartt D. A. et al, J. Physiol (London) 352; 375–384, 1984).

Cellular cyclic nucleotide levels can also be increased by exogenous addition of cyclic nucleotide analogues to which cells are permeable. Cells are not permeable to cyclic AMP or cyclic GMP, thus the exogenous addition of these compounds does not elevate cellular cyclic nucleotide levels.

It is know that exogenous 8-bromo cyclic AMP, dibutyryl cyclic AMP or adenosine 3'-5'-cyclic phosphorothioate stimulate protein secretion from lacrimal gland tissue pieces or cells in vitro, but 8-bromo cyclic GMP does not. (Friedman Z. Y. et al, Biochemica et Biophysica Acta 675: 40–45, 1981: Jahn R. et al, Eur. J. Biochem 126: 623–629, 1982; Mauduit P. et al, Am. J. Physiol J. 246; C37–C44, 1984; Dartt D. A. et al, J. Physiol (London) 352; 375–384, 1984.)

What is needed are agents which will stimulate tear secretion upon topical administration to the ocular surface. A topical mode of administration has several advantages. It eliminates the need for injections in patents with dry eye disorders, thereby decreasing systemic effects, cost of therapy, and the amount of drug needed.

Accordingly, it is an object of this invention to provide an improved method for stimulating tear secretion by topical administration. It is another object of this invention to provide an improved method of stimulating lacrimal gland secretion by topical application of compounds to the ocular surface. It is also an object to provide an improved method for the treatment of dry eye disorders. Another object of the present invention is to facilitate the treatment of dry eye disorders without systemic therapy such as injection. A further object is to provide an improved agent for topical application to improve eye comfort. It is another object of the present invention to provide an agent for topical application to enhance contact lens wear and comfort. A further object is to provide a method for increasing the amount of the tear fluid produced by lacrimal gland tissue. Other objects of the invention will in part be obvious and will in part appear hereinafter.

SUMMARY OF THE INVENTION

In accordance with the invention, it has been found that agents including phosphodiesterase inhibitors and cyclic nucleotide analogues that increase intracellular cyclic nucleotide levels in lacrimal gland tissue effectively stimulate tear secretion when applied topically to the eye. This method for stimulating tear secretion is useful in the treatment of dry eye disorders, and it facilitates such treatment by eliminating the need for injections. Also, a corresponding preparation has been found which can be applied topically to stimulate lacrimal gland secretion. The preparation contains a phosphodiesterase inhibitor or a cyclic nucleotide analogue and a preservative. The preparation typically also contains a physiologically compatible vehicle.

The method involves topical administration to the ocular surface of compounds that increase intracellular cyclic nucleotide levels, thereby stimulating tear secretion. These compounds may include phosphodiesterase inhibitors such as 3-isobutyl-1-methylxanthine (IBMX), and theophylline, as well as caffeine and theobromine and other methylxanthine phosphodiesterase inhibitors that increase cyclic nucleotide levels in lacrimal gland tissue. The compounds also include cyclic nucleotide analogues such as 8-bromo cAMP, dibutyrl cAMP, adenosine 3'-5'-cyclic phosphorothioate, 8-bromo cGMP, and other cyclic nucleotide derivatives. These compounds may be used alone or in combination with one another. The compounds deemed preferred are IBMX and 8-bromo cAMP.

Several modes of topical administration may be used in the practice of the invention. For example, the compounds may be administered topically to the eye as a drop, or within ointments, gels, or liposomes. Further, compounds may be infused into the tear film by means of a pump-catheter system. In other embodiments the compounds are attached to and/or incorporated into or carried by contact lenses or contained within continuous or other selective-release devices including membranes, and thereby contact the ocular surface.

The development of the foregoing agents that are effective in stimulating lacrimal secretion when applied topically to the eye is unexpected for several reasons. First, the main lacrimal gland is not exposed to the surface of the eye and lies separated from the ocular surface by a relatively great diffusion distance. The main lacrimal gland is connected to the surface only through a series of microscopic ducts. Therefore, while drugs injected vascularly can reach the main lacrimal gland parenchyma, it is considered unlikely that topically applied drugs will do so. Second, although there are microscopic nests of accessory lacrimal gland tissue within the conjunctiva, one would expect that insufficient lacrimal tissue mass will preclude the success of an approach that seeks to act merely on the accessory glands.

BRIEF DESCRIPTION OF THE DRAWINGS

FIGS. 1A, 1B and 1C are graphs of the osmolality of tear samples as a function of time taken from a rabbit eye treated with buffer solution and, subsequently, the same eye treated in accordance with the invention with buffer solution containing IBMX in concentrations of respectively 0.3 mM, 1.0 mM, and 3.0 mM.

FIGS. 2A, 2B, and 2C and 2D are graphs of the osmolality of tear samples as a function of time taken from a rabbit eye treated with buffer solution and, subsequently, the same eye treated in accordance with the invention with buffer solution containing theophylline in concentrations of 3.0 mM, 10.0 mM, 30.0 mM, and 60.0 mM.

FIG. 3A is a graph of the osmolality of tear samples as a function of time taken from a rabbit eye treated with buffer solution and, subsequently, the same eye treated in accordance with the invention with buffer solution containing $3 \times 10^{-6}$ M glucagon.

FIG. 3B is a graph of the osmolality of tear samples as a function of time taken from a rabbit eye treated with buffer solution and, subsequently, the same eye treated in accordance with the invention with buffer solution containing 0.5 mM of IBMX.

FIG. 3C is a graph of the osmolality of tear samples as a function of time taken from a rabbit eye treated with buffer solution and, subsequently, the same eye treated in accordance with the invention with buffer solution containing $3 \times 10^{-6}$ M glucagon and 0.5 mM IBMX.

FIGS. 4A, 4B and 4C represent results obtained from further practice of the invention with rabbits. In particular, FIGS. 4A, 4B and 4C are graphs of the osmolality of tear samples as a function of time taken from a rabbit eye treated with buffer solution and, subsequently, the same eye treated in accordance with the invention with buffer solution containing 8-bromo cAMP in concentration of 1.0 mM, 3.0 mM, and 10.0 mM.

FIGS. 5A, 5B and 5C represent results obtained from further practice of the invention with rabbits. In particular, FIGS. 5A, 5B and 5C are graphs of the osmolality of tear samples as a function of time taken from a rabbit eye treated with buffer solution and, subsequently, the same eye treated in accordance with the invention with buffer solution containing 8-bromo cGMP in concentrations of 1.0 mM, 3.0 mM, and 10.0 mM.

DESCRIPTION OF THE INVENTION

Figure 1A:
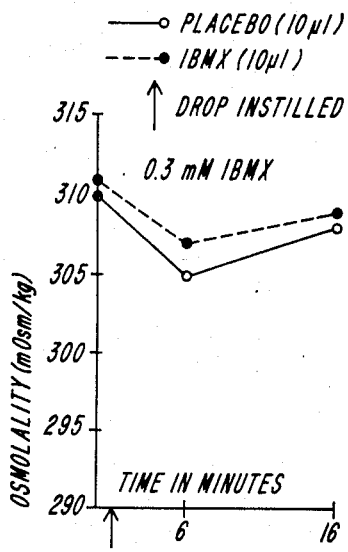
FIGS. 1A, 1B, and 1C represent results obtained from practice of the invention with rabbits. In particular.

In accordance with the invention, tear secretion is stimulated with topically applied agents including phosphodiesterase inhibitors, and cyclic nucleotide analogues that increase intracellular cyclic nucleoticle levels in lacrimal gland tissue. More particularly, these phosphodiesterase inhibitors can include but are not limited to methylxanthines including IBMX and theophylline. By way of specific example, the cyclic nucleotide analogues can include but are not limited to 8-bromo cyclic AMP, and 8-bromo cyclic GMP. A further practice employs a combination of a phosphodiesterase inhibitor with a gastrointestinal hormone and/or biologically active peptide that activates vasoactive intestinal peptide or malantropin receptor.

A preparation according to the invention can, by way of non-limiting illustration, be applied to the eye in animals and humans as a drop or within ointments, gels, or liposomes. Further, the compounds may be infused into the tear film via a pump-catheter system. In other embodiments, the compounds can be contained within continuous or other selective-release devices, for example, membranes, such as but not limited to those used in the Ocusert ® system (Alza Corp., Palo Alto, CA). As a further specific example, the compounds can be attached to or carried by and/or contained within contact lenses that are placed on the eye. In general, it is desired that the mode of application be such that the compounds enter the tear film or make contact with the surface of the eye.

In vivo examples in accordance with the invention were conducted on rabbits with dry eyes. The dry eye disorder is created by surgically closing the duct that carries fluid from the main lacrimal gland to the tear film, and surgically removing the nictitans and harderian glands. This leaves intact only the accessory glands that lie on the ocular surface. These rabbits develop increased tear film osmolality soon after the operation, a finding that is understood to be due to decreased tear production, and that is characteristic of dry eye. It is recognized that results of ophthalmologic tests using rabbits has close correlation with humans and therefore the results carry over to humans.

The effect of topically applied isotonic buffer solution with and without methylxanthine phosphodiesterase inhibitors or cyclic nucleaotide analogues on tear film osmolality was studied in the dry eye rabbit. All test drops were ten microlitres ($\mu$l) in volume. Tear samples were taken with a micropipette system, in the manner described in the article entitled "Osmolarity of Tear Microvolumes in Keratoconjunctivities Sicca", by Gilbard et al, Arch Ophthalmol 96:677, 1978. Osmolality was measured by freezing-point depression.

The following protocol was used to test the effects of topically applied methylxanthines or cyclic nucleotide analogues. At zero time a tear sample was taken for measurement of osmolality. At one minute the test drop was instilled. At six and at sixteen minutes, tear samples were taken for osmolality measurements. The above sequence was repeated several times, each time after a wait of five minutes after the sixteen-minute sample, to test additional drops.

Figure 1B:
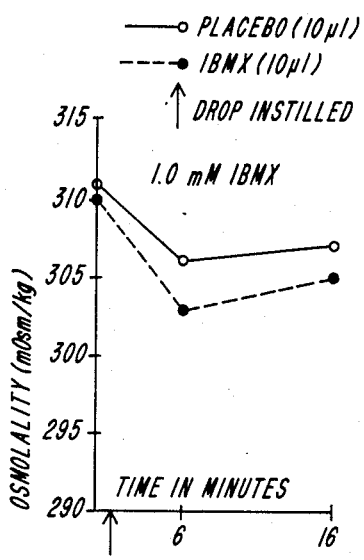
Figure 1C:
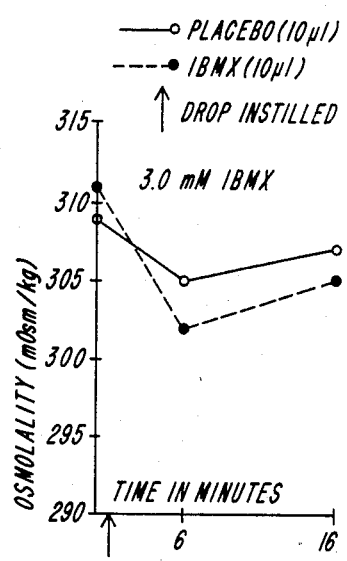
Figure 2A:
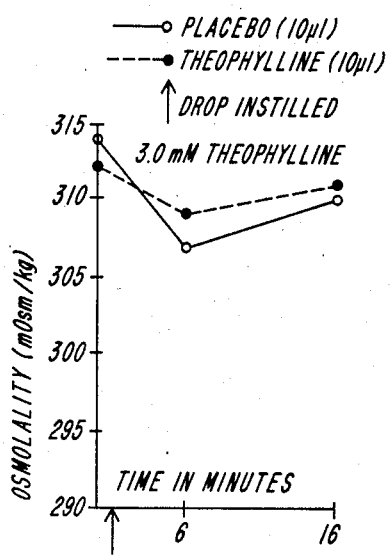
FIGS. 2A, 2B, 2C, and 2D represent results obtained from practice of the invention with rabbits. In particular.
Figure 2B:
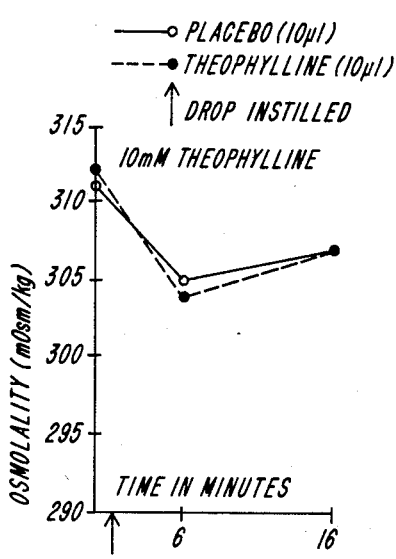
Figure 2C:
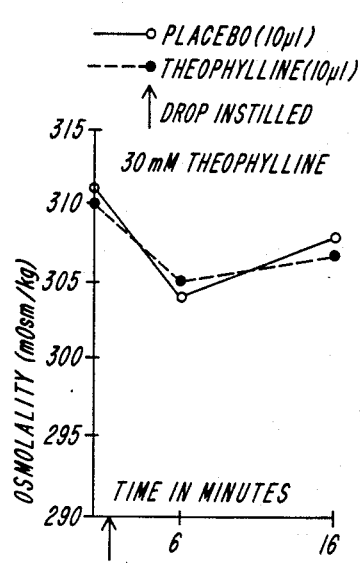
Figure 2D:
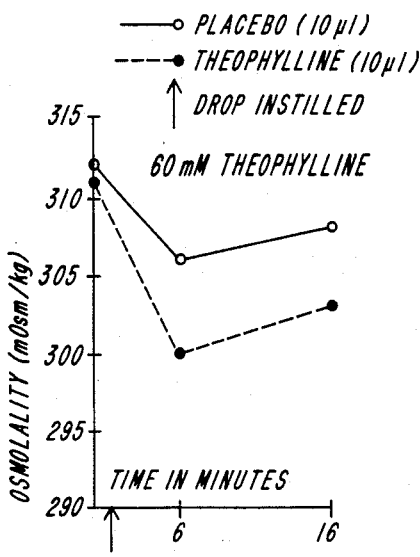
Figure 3A:
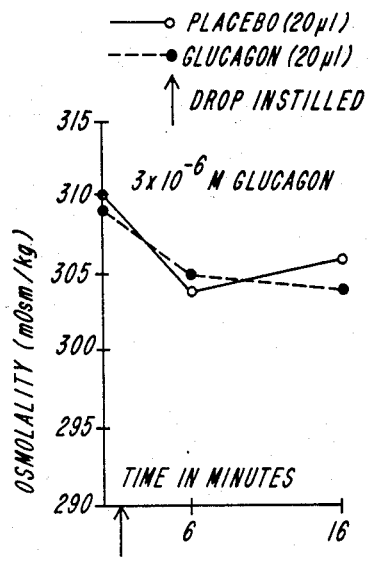
FIGS. 3A, 3B, and 3C represent results obtained from further practice of the invention with rabbits.
Figure 3B:
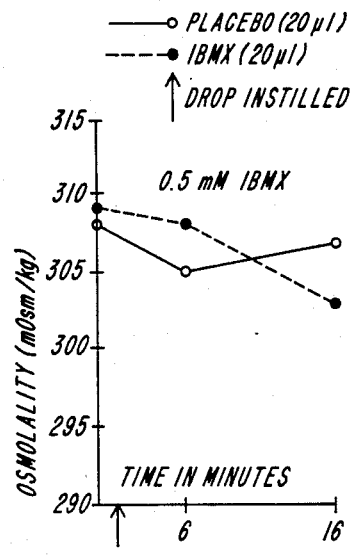
Figure 3C:
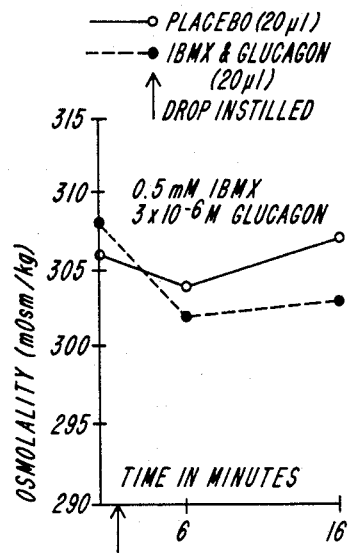

The following drops were instilled in the test eye and after each such instillation test samples were taken as stated: (1) buffer solution, (2) buffer solution containing a methylxanthine or cyclic nucleotide analogue at a low dose, (3) buffer solution, (4) buffer solution containing a methylxanthine or cyclic nucleotide analogue at a moderate dose, (5) buffer solution, and (6) buffer solution containing a methylxanthine or cyclic nucleotide analogue at a higher dose. In addition, one example (FIG. 2) also included the following: (7) buffer solution, and 8) buffer solution containing a methylxanthine at a still higher dose. The results are shown in FIGS. 1A, 1B, and 1C, FIGS. 2A, 2B, 2C, and 2D FIGS. 3A, 3B, and 3C FIGS. 4A, 4B and 4C, and FIGS. 5A, 5B and 5C; where FIGS. 1, 2, 3, 4 and 5 each represent results obtained from the same rabbit.

FIG. 1 represents results obtained with IBMX. The concentrations of IBMX given in the 10 $\mu$l drops were: (A) 0.3 mM, (B) 1.0 mM, and (C) 3.0 mM. As shown in FIG. 1, buffer solution containing IBMX lowers the tear film osmolality more effectively than buffer alone. The figure also indicates a dose-dependent decrease in tear film osmolality, and the decrease was strikingly more pronounced than the effect of the buffer alone. This reflects an IBMX stimulated dose-dependent increase in tear secretion.

FIG. 2 represents results obtained with theophylline. The concentrations of theophylline given in the 10 $\mu$l drops were: (A) 3.0 mM, (B) 10.0 mM, (C) 30.0 mM, and D) 60.0 mM. As shown in FIG. 2, buffer solution containing 60.0 mM theophylline lowers tear film osmolality more effectively than buffer alone. This reflects a theophylline stimulated increase in tear secretion.

FIG. 3 represents results obtained with IBMX, glucagon, and a combination of IBMX and glucagon. Glucagon is a gastrointestinal peptide which upon topical administration to the ocular surface produces a dose-dependent decrease in tear film osmolality. IBMX and glucagon were tested in combination to determine if the two have a synergistic effect on tear film osmolality. The concentrations given in 20 $\mu$l drops were as follows: (A) $3 \times 10^{-6}$M glucagon, (B) 0.5 mM of IBMX, (3) $3 \times 10^{-6}$M glucagon and 0.5 mM IBMX. As shown in FIG. 3, the combination of glucagon and IBMX lowers tear film osmolality more effectively than either glucagon or IBMX alone.

FIG. 4 represents results obtained with 8-bromo cAMP. The concentrations of 8-bromo cAMP given in the ten microliter drops were (a) 1.0 mM, (b) 3.0 mM, and (c) 10.0 mM. As shown in FIG. 4, buffer solution containing 8-bromo cAMP lowers tear film osmolality more effectively than buffer alone. This reflects an 8-bromo cAMP stimulated increase in tear secretion.

FIG. 5 represents results obtained with 8-bromo cGMP. The concentrations of 8-bromo cGMP given in the ten microliter drops were (a) 1.0 mM, (b) 3.0 mM, and (c) 10.0 mM. As shown in FIG. 5, buffer solution containing 8-bromo cGMP lowers tear film osmolality more effectively than buffer alone. This reflects an increase in tear secretion stimulated by the 8-bromo cGMP.

In further accordance with the invention, a topical tear-stimulation preparation is made by combining a phosphodiesterase inhibitor or cyclic nucleotide analogue that increases cyclic nucleotide levels in lacrimal gland tissue with an appropriate preservative. The preparation typically also contain a physiologically compatible vehicle, as those skilled in the art can select using conventional criteria. The vehicles may be selected from the known ophthalmic vehicles which include, but are not limited to water, polyethers such as polyethylene glycol, polyvinyls such as polyvinyl alcohol and povidone, cellulose derivative such as methylcellulose and hydroxypropyl methylcellulose, petroleum derivatives such as mineral oil, white petrolatum, animal fats such as lanolin, vegetable fats such as peanut oil, polymers of acrylic acid such as carboxypolymethylene gel, polysaccharides such as dextrans, glycosaminoglycans such as sodium hyaluronate and salts such as sodium chloride and potassium chloride. One preferred vehicle is the non-toxic ophthalmic preparation which has the following composition: about 22.0 to 43.0 millimoles of potassium per liter; about 29.0 to 50.0 millimoles of bicarbonate per liter; about 130.0 to 140.0 millimoles of sodium per liter; and about 118.0 to 136.5 millimoles of chloride per liter.

Phosphodiesterase inhibitor preservatives include, but are not limited to, sorbic acid, chlorhexidine, benzalkonium chloride and thimerosal. Preservatives for cyclic nucleotide analogue include, but are not limited to, chlorohexidine. Other preservatives may be appropriate, as those skilled in the art can select using conventional criteria. Stated generally, both the vehicle and preservative are to be physiologically compatible with the phosphodiesterase inhibitors and cyclic nucleotide analogues and are not to inactivate the secretion-stimulating activity of these compounds.

In accordance with the invention, one example of the preparation contains IBMX, the foregoing non-toxic ophthalmic preparation as a vehicle, and chlorohexidine for installation in the eye in drop form. Another example consists 8-bromo cAMP, the foregoing non-toxic ophthalmic preparation and chlorohexidine.

It will thus be seen that the objects set forth above, among those made apparent from the preceding description, are efficiently attained. Since certain changes may be made in carrying out the above method, and in formulating the foregoing preparation, without departing from the scope of the invention, it is intended that all matter contained in the above description shall be interpreted as illustrative and not in a limiting sense.

Accordingly, the invention may be embodied in other specific forms without departing from the scope or spirit thereof.

What is claimed is:

1. A method of stimulating in vivo fluid secretion from human accessory lacrimal glands comprising the step of topical administration to the ocular surface of a therapeutically effective amount of a preparation which includes a compound that causes an increase in the intracellular cyclic nucleotide levels in said accessory lacrimal glands wherein said compound is a phosphodiesterase inhibitor.

2. The method of claim 1 wherein said phosphodiesterase inhibitors are selected from a group consisting of methylxanthines, caffeine, theophylline, theobromine, and derivatives thereof.

3. The method of claim 2 wherein said preparation further comprises glucagon.

4. The method of claim 2 wherein said phosphodiesterase inhibitor comprises 3-isobutyl-1-methylxanthine.

5. The method of claim 1 wherein said topical administration comprises infusion of said preparation from a device selected from a group consisting of a pump-catheter system, a selective release device, and a contact lens.

6. The method of claim 1 wherein said preparation for topical administration comprises dispersion of said compound in a carrier vehicle selected from a group consisting of drops of liquid, gels, ointments, and liposomes.

* * * * *

UNITED STATES PATENT AND TRADEMARK OFFICE
CERTIFICATE OF CORRECTION

PATENT NO.   :  4,753,945
DATED        :  June 28, 1988
INVENTOR(S)  :  Jeffrey P. Gilbard et al.

It is certified that error appears in the above-identified patent and that said Letters Patent is hereby corrected as shown below:

At Column 2, line 7 delete "know" and insert --known--.

At Column 2, line 19 delete "patents" and insert --patients--.

At Column 6, line 8 delete "contain" and insert --contains--.

Signed and Sealed this

Sixth Day of June, 1989

Attest:

DONALD J. QUIGG

Attesting Officer

Commissioner of Patents and Trademarks